United States Patent [19]

Masukawa

[11] Patent Number: 5,053,325

[45] Date of Patent: Oct. 1, 1991

[54] SILVER HALIDE COLOR PHOTOGRAPHIC LIGHT-SENSITIVE MATERIAL

[75] Inventor: Toyoaki Masukawa, Hino, Japan

[73] Assignee: Konica Corporation, Tokyo, Japan

[21] Appl. No.: 592,784

[22] Filed: Oct. 2, 1990

[30] Foreign Application Priority Data

Oct. 7, 1989 [JP] Japan .................................. 1-262791

[51] Int. Cl.$^5$ ................................................ G03C 7/36
[52] U.S. Cl. .......................................... 430/557; 430/556
[58] Field of Search ................................ 430/556, 557

[56] References Cited

U.S. PATENT DOCUMENTS

| | | | |
|---|---|---|---|
| 3,393,040 | 7/1968 | Verbrugghe et al. | 430/556 |
| 4,032,347 | 6/1977 | Van Poucke et al. | 430/557 |
| 4,529,691 | 7/1985 | Renner et al. | 430/557 |
| 4,774,181 | 9/1988 | Ravindran et al. | 430/557 |

FOREIGN PATENT DOCUMENTS

| | | |
|---|---|---|
| 2169879 | 9/1973 | France . |
| 2217724 | 9/1974 | France . |
| 1191131 | 10/1989 | Japan . |

*Primary Examiner*—Richard L. Schilling
*Attorney, Agent, or Firm*—Frishauf, Holtz, Goodman & Woodward

[57] ABSTRACT

A silver halide photographic light-sensitive material is disclosed, which contains a novel yellow coupler in its silver halide emulsion layer. The yellow coupler is represented by the following Formula I:

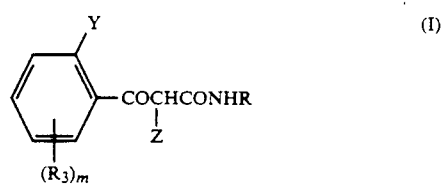

wherein Y is a hydrogen bond donating group; R is an alkyl group, an aryl group or a heterocyclic group; $R_3$ is a halogen atom, a hydroxyl group, a nitro group or a monovalent organic group; m is an integer of 0 to 4, provided that the groups represented by $R_3$ may be the same or different when m is 2 or more; and Z is a hydrogen atom or a substituent capable of splitting off upon reaction with the oxidation product of an aromatic primary amine color developing agent.

9 Claims, No Drawings

SILVER HALIDE COLOR PHOTOGRAPHIC LIGHT-SENSITIVE MATERIAL

FIELD OF THE INVENTION

The present invention relates to a silver halide color photographic light-sensitive material containing a new yellow coupler giving high optical density, excellent color reproducibility and excellent image preservability.

BACKGROUND OF THE INVENTION

In the current color photographic methods, based on the subtractive color process, it is usually the case where a yellow coupler is added in a blue-sensitive silver halide emulsion layer, a magenta coupler is added in a green-sensitive silver halide emulsion layer and a cyan coupler is added in a red-sensitive silver halide emulsion layer.

The current color photography is based on the reaction in which these couplers are coupled with the oxidation product of the aromatic primary amine-based developing agent in the developer by color development and form azomethine and indoaniline dyes in respective photographic layers.

For obtaining good color reproducibility, it is desirable that the yellow color dye formed by development has an absorption spectrum in the blue region alone while showing no undesirable absorption in the green or red region, the magenta color dye has an absorption spectrum mainly in the green region while showing no undesirable absorption in the adjoining blue or red region, and the cyan color dye shows no undesirable absorption in the green or blue region.

Traditionally, benzoyl acetanilide type couplers and pivaloyl acetanilide type couplers have been in practical use as yellow couplers for negative films and papers, respectively, but further improvements are desired in absorption spectrum and light fastness.

In the case of negative films, it is possible to correct undesirable absorption by masking. On the other hand, no improvement is possible by such a means in the use for color papers; therefore, it is more important to improve the coupler itself. Also, there are some other methods; for example, U.S. Pat. No. 4,774,181 describes a coupler that releases a fluorescent substance, which is based on the idea that the broadness of the absorption spectrum of coloring dye is compensated by some luminescence.

However, none of the conventional fluorescent dyes has satisfactory fastness, and further improvements are needed.

SUMMARY OF THE INVENTION

It is an object of the present invention to provide a yellow coupler that offers reduction of undesirable absorption and significant improvement in color reproducibility. It is another object of the present invention to provide a yellow coupler with a high optical density and improved light-fastness. It is yet another object of the present invention to provide a new yellow coupler that permits partial masking of absorption spectrum by the possession of fluorescence of the yellow image formed. It is still another object of the present invention to provide a silver halide color photographic light-sensitive material that is excellent in color reproducibility and image preservability.

These objects of the present invention can be accomplished with a silver halide color photographic material comprising a support and a silver halide emulsion layer containing a yellow coupler represented by the following Formula I:

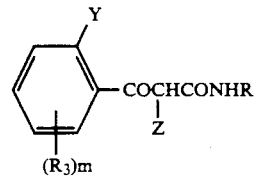

Formula I wherein Y is a hydrogen bond-donating group; R is an alkyl group, an aryl group or a heterocyclic group; $R_3$ is a halogen atom, hydroxyl group, nitro group, or a monovalent organic group; m is an integer of 0 to 4, provided that the groups represented by $R_3$ may be the same or different when m is 2 or more; and Z is a hydrogen or a substituent capable of splitting off upon reaction with the oxydation product of an aromatic primary amine color developing agent.

DETAILED DESCRIPTION OF THE INVENTION

Preferenced ones of the coupler of the invention having those hydrogen bond-donating group are represented by the following formula II wherein the hydrogen bond-donating group is represented by $-XR_1$.

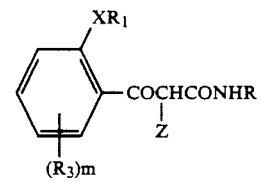

Formula II wherein R, $R_3$, Z and m have the same definitions as with Formula I; X represents $-NH-$ or $-O-$; when X represents $-NH-$, $R_1$ represents a group represented by $-COR_4$ or $-SO_2R_4$, and $R_4$ represents an alkyl group, an aryl group, an alkylamino group, a dialkylamino group, an arylamino group, an alkoxy group or an aryloxy group; when X represents $-O-$, $R_1$ represents a hydrogen atom.

Examples of the alkyl group represented by $R_4$ include normal or branched alkyl groups such as methyl, ethyl, propyl, s-butyl, t-butyl, n-hexyl, decyl and dodecyl, and it may be a cycloalkyl group, a cyclopentyl group, a cyclohexyl group or an adamantyl group.

These alkyl groups may have a substituent. Examples of preferred substituents include halogen atoms such as a fluorine atom and a chlorine atom. Also preferred are those substituted with an aryl group such as a phenethyl group, a phenylpropyl group and a p-butanamidophenylpropyl group.

Also, the aryl group represented by $R_4$ may be an unsubstituted aryl group such as a phenyl group or a naphthyl group, and the phenyl group and naphthyl group may have a substituent.

Examples of such substituents include a halogen atom, a nitro group, a hydroxy group, an alkyl group, an alkoxy group, an alkylamido group, an alkylsulfonamido group, an arylamido group, an arylsulfonamido group, an alkylcarbamoyl group, an arylcarbamoyl group, an alkoxycarbonyl group, an aryloxycarbonyl group, an alkanoyloxy group and an arylcarbonyloxy group.

More specific examples include a p-chlorophenyl group, a pentafluorophenyl group, a p-nitrophenyl group, an m-hydroxyphenyl group, a tolyl group, a trimethylphenyl group, a p-methoxyphenyl group, a 2-butoxy-5-octylphenyl group, a p-dodecyloxyphenyl group, a p-pivaloylamidophenyl group, an n-pentaneamidophenyl group, a pentafluoropropionamidophenyl group, a p-methanesulfonamidophenyl group, an m-butanesulfonamidophenyl group, a p-benzamidophenyl group, a p-tolylamidophenyl group, a benzenesulfonamidophenyl group, a p-dodecylbenzenesulfonamidophenyl group, a 2-octyloxy-5-oxylbenzenesulfonamidophenyl group, an o-(butylcarbamoyl)phenyl group, a p-(phenylcarbamoyl)phenyl group, a p-(p-methoxyphenylcarbamoyl)phenyl group, an o-ethoxycarbonylphenyl group, a p-butoxycarbonylphenyl group, an acetoxyphenyl group, a hexanoyloxyphenyl group and a benzoyloxy group.

Examples of the alkylamino group or dialkylamino group include an ethylamino group, a dimethylamino group, a butylamino group and a diethylamino group.

Examples of the arylamino group include substituted or unsubstituted arylamino groups such as an anilino group, a p-methoxyanilino group and an m-nitriloanilino group. Examples of the alkoxy group include substituted or unsubstituted alkoxy groups; unsubstituted alkoxy groups such as a methoxyl group, an ethoxy group, a butoxy group or a hexadecyloxy group. Examples of the aryloxy group include substituted or unsubstituted aryloxy groups such as a phenoxy group, chlorophenoxy group or methylphenoxy group.

Examples of the alkyl group represented by R in Formulas I and II include unsubstituted alkyl groups such as methyl, ethyl, butyl, t-butyl, 2-ethylhexyl and dodecyl; substituted alkyl groups such as hydroxyethyl, benzyl and phenethyl; and cycloalkyl groups such as cyclopentyl and cyclohexyl.

Examples of the heterocyclic group represented by R include a 3-pyridyl group, a 2-pyridyl group, a 2-pyrimidinyl group, a 2-thiazolyl group, a 2-furyl group, a 5-s-triazolyl group, a 2-oxazolyl group, a 2-benzoxazolyl group, a 2-benzothiazolyl group and a 2-benzimidazolyl group.

Examples of the aryl group represented by R include a phenyl group and a naphthyl group, in which groups represented by

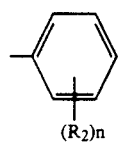

are particularly preferable.
Couplers of the invention are preferably represented by the following formula III.

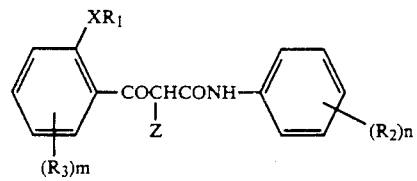

Formula III wherein X, $R_1$, $R_3$, Z and m have the same definitions as with Formula I or II; $R_2$ represents a halogen atom or a monovalent organic group; n represents an integer of 0 to 5; when n is 2 or more, $R_2$ may represent two or more different groups.

In Formula I, II or III, examples of the monovalent organic group represented by $R_2$ or $R_3$ include an alkyl group, an aryl group, an alkoxy group, an aryloxy group, an alkylamido group, an arylamido group, an alkylsulfonamido group, an arylsulfonamido group, an alkylcarbamoyl group, an arylcarbamoyl group, an alkoxycarbonyl group, an aryloxycarbonyl group, an alkanoyloxy group, and arylcarbonyloxy group and a dialkylamino group, with preference given to those groups mentioned as substituents for the aryl group for $R_4$ described above, with more preference given to alkoxy groups such as a methoxy group, an ethoxy group and a hexadecyloxy group; alkylamido groups such as lauroylamido group, 2,4-di-t-amylphenoxybutanamido group and α-methyl-β-(n-dodecylsulfonyl)propionamido group; and substituted or unsubstituted alkyloxycarbonyl groups such as dodecyloxycarbonyl group and α-(n-dodecyloxycarbonyl)ethoxycarbonyl group.

With Formulas I to III, atoms or groups (split-off group) represented by Z and being capable of splitting off upon reaction with the oxydation product of a color developing agent are widely known in the photographic art, and examples of which include halogen atoms, an alkoxy group, an aryloxy group, an arylthio group, 5- or 6-membered nitrogen-containing heterocyclic group, and of which those preferred are a chlorine atom and groups represented by the following Formula IV or V.

Formula IV

wherein $R_5$ represents an aryl group or heterocyclic group possibly having a substituent group.

Typical examples of such groups include a phenoxy group, a 4-nitrophenoxy group, a 4-carboxyphenoxy group, a 3-carboethoxyphenoxy group, a 4-phenoxycarbonylphenoxy group, a 2-(3-carboxypropionamido)-phenoxy group, a 4-(4-benzyloxyphenylsulfonyl)-phenoxy group and a 1-morpholinoxy group.

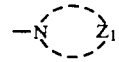

Formula V $Z_1$ represents a non-metallic atoms group necessary for forming a 5- or 6-membered heterocyclic group together with N. Examples that form this group include

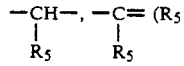

is a hydrogen atom or a substituent group), —CO—, —NH—, —N=, —O—, —S— and —$SO_2$.

Typical examples of those represented by Formula V include an N-benzylhydantoinyl group, a 2-phenylcarbamoyl--1-imidazolyl group, a 3,5-diketo-1-benzyl--phenyl-1,2,4-triazolidine-1-yl group, a 2,5-diketo-3-benzyl-4-ethoxyimidazolidine and a benzotriazole.
Examples of the yellow coupler of the present invention are given below, but the invention is not by any means limited thereby.
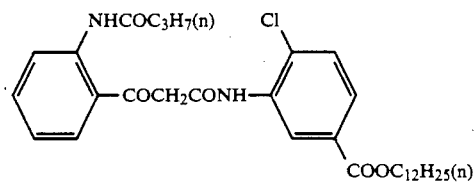
1.
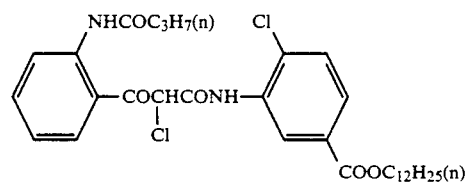
2.
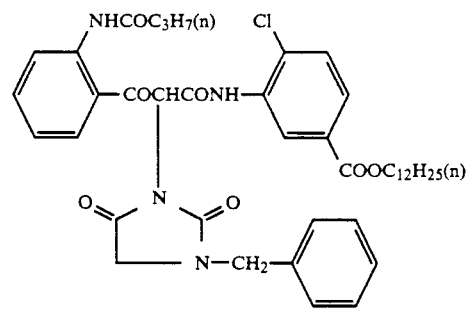
3.
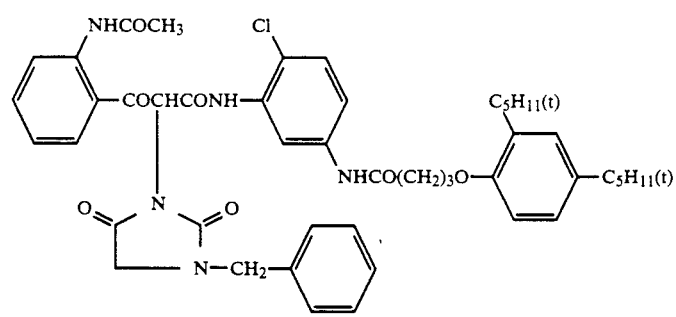
4.
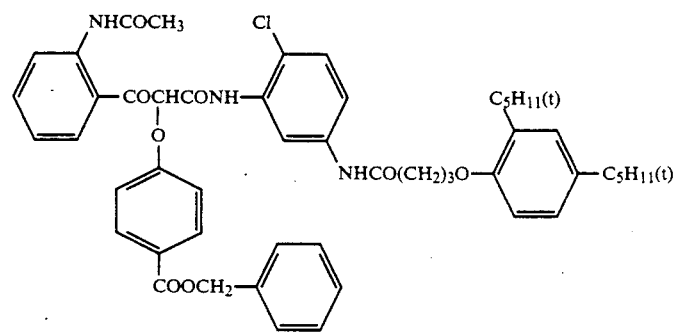
5.

-continued
6.
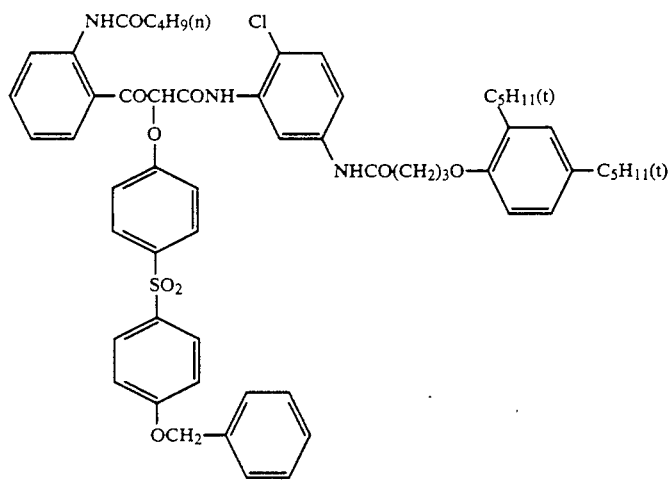
7.
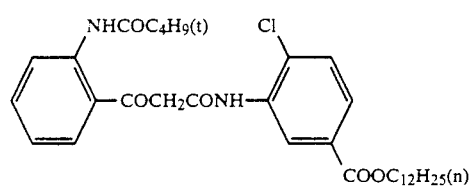
8
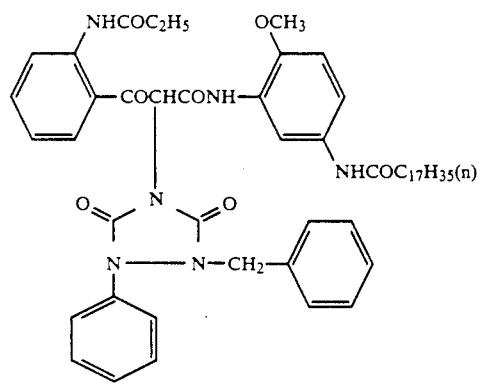
9
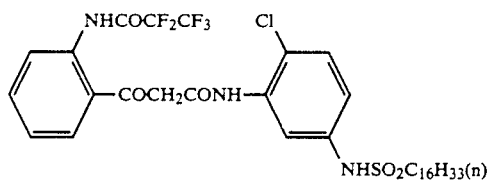
10
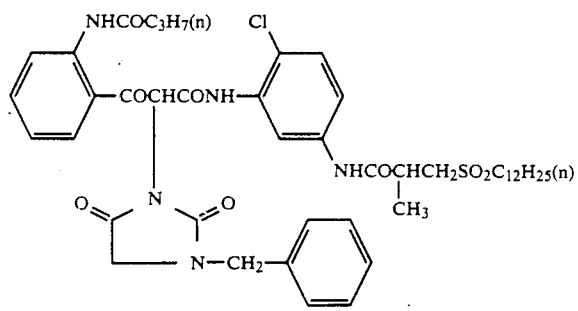

11.
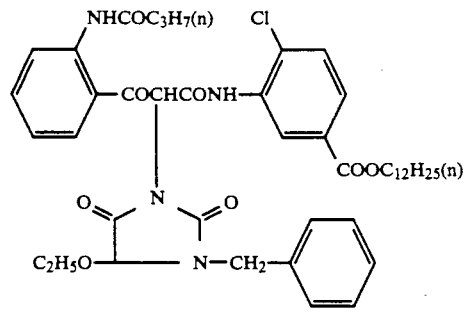
12.
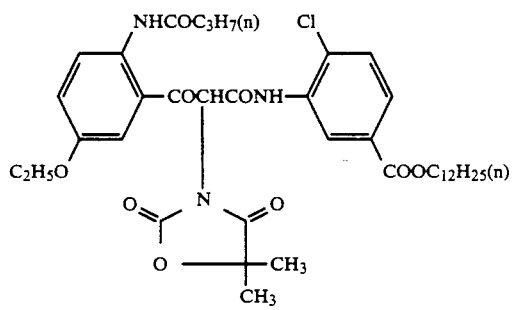
13.
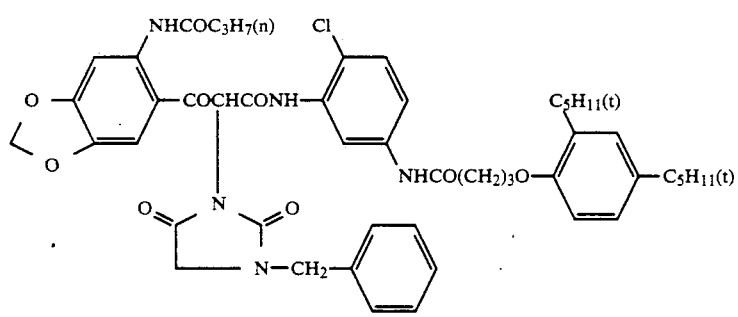
14.
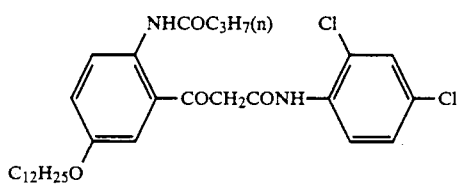
15.
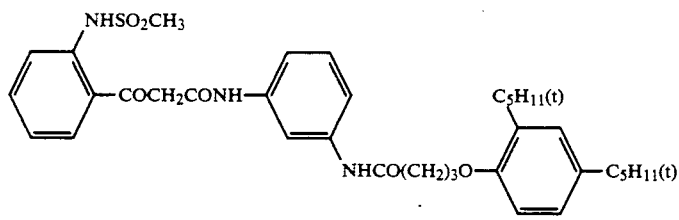
16.
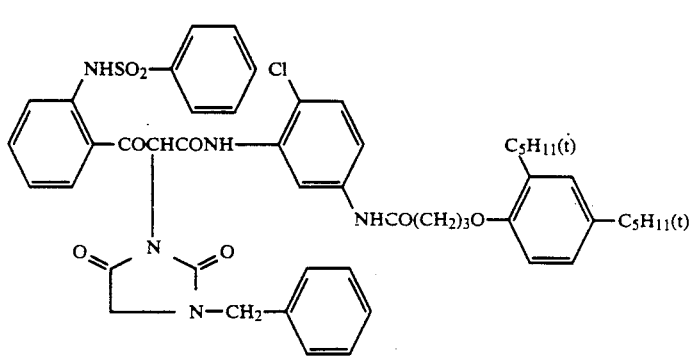

-continued
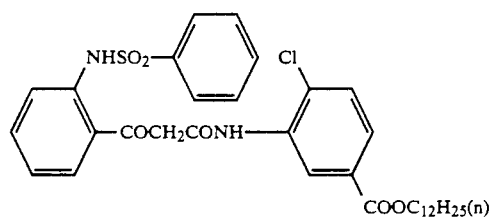
17.
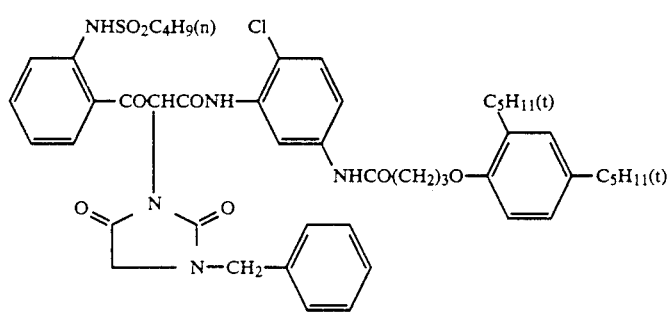
18.
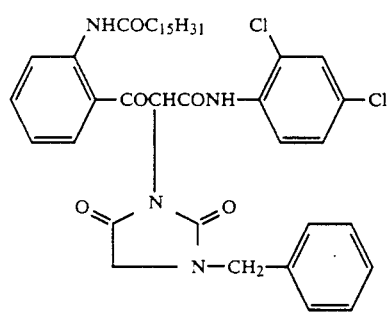
19.
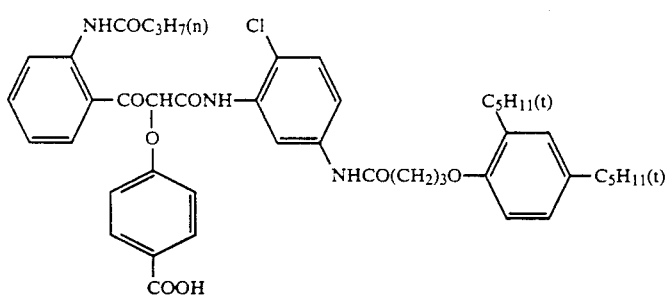
20.
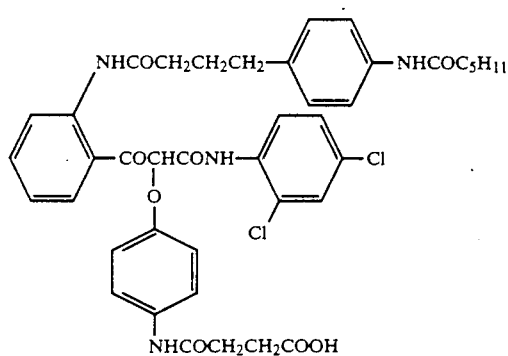
21.

-continued
22.
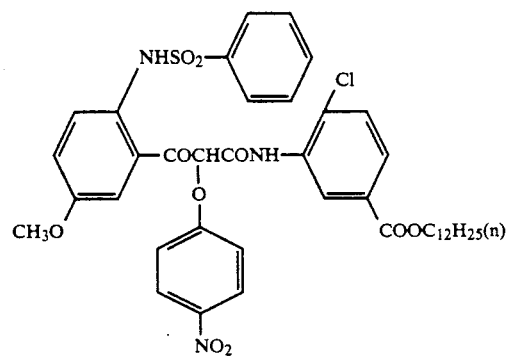
23.
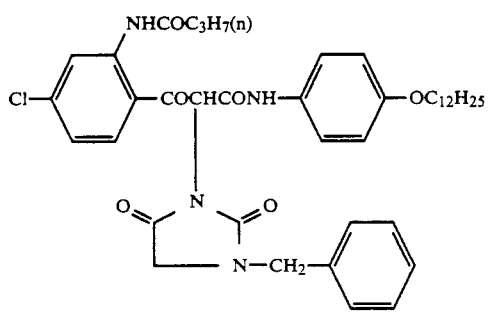
24.
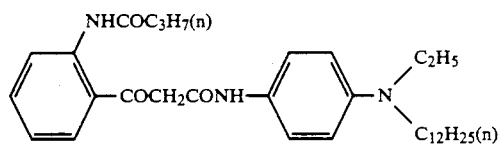
25.
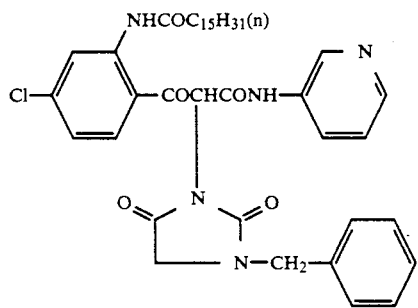
26.
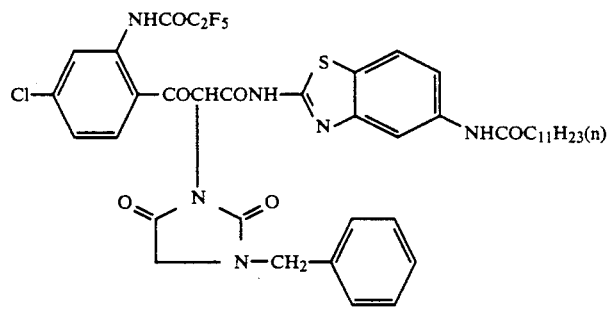
27.
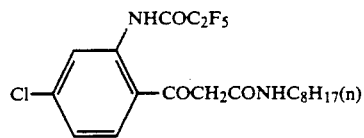

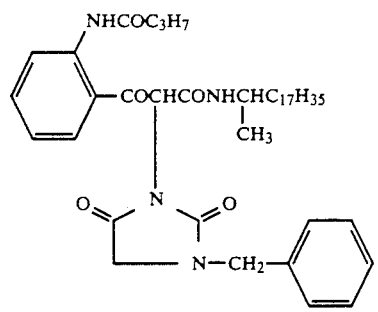
28.
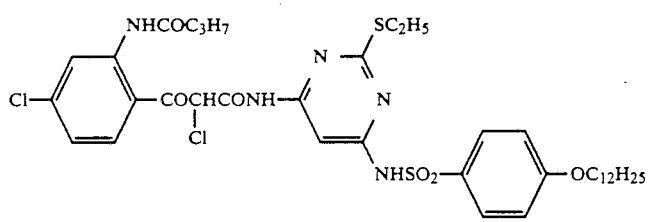
29.
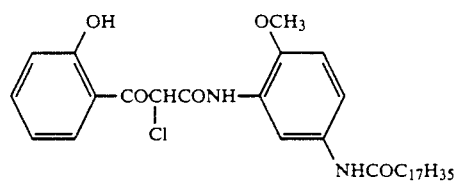
30.
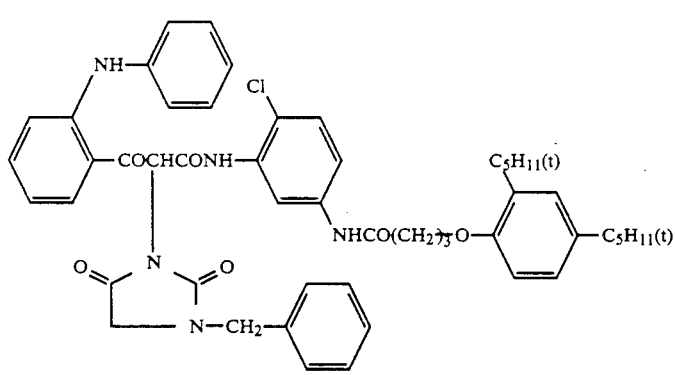
31.
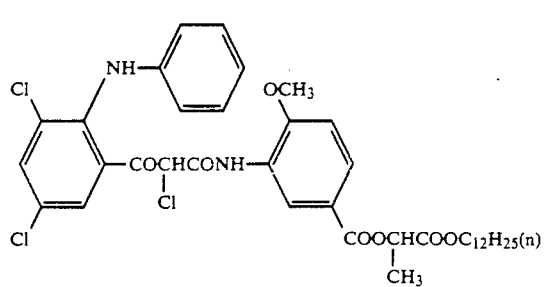
32.

-continued
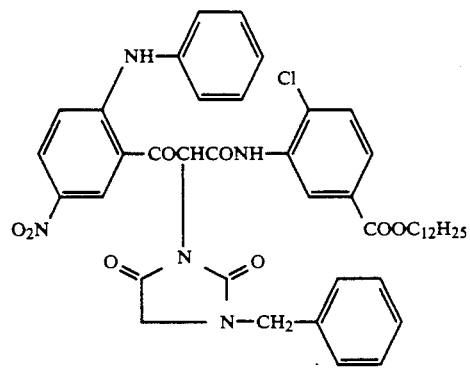
33.
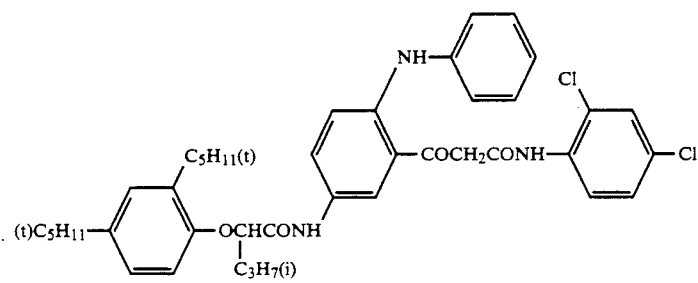
34.
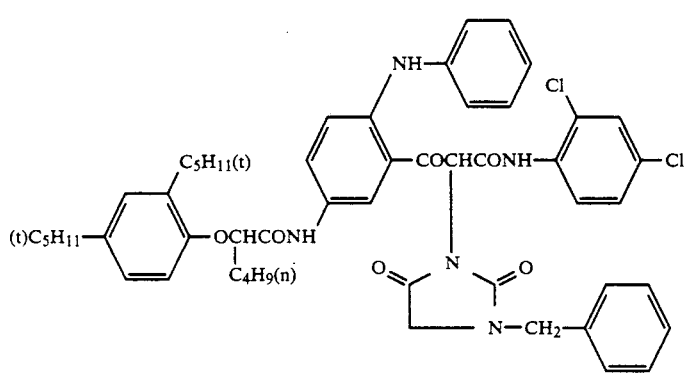
35.
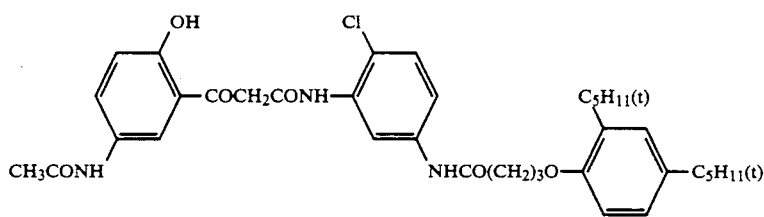
36.
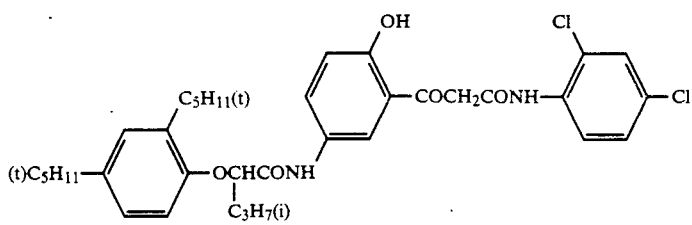
37.

-continued

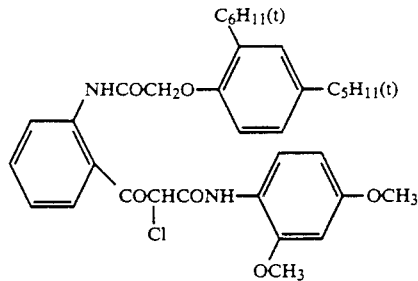 38.

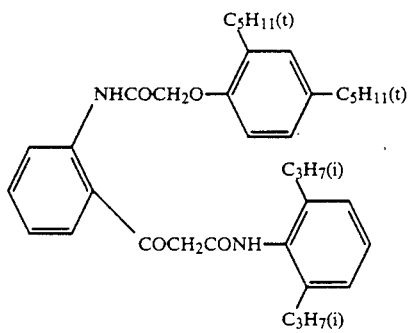 39.

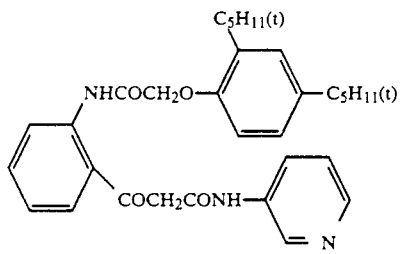 40.

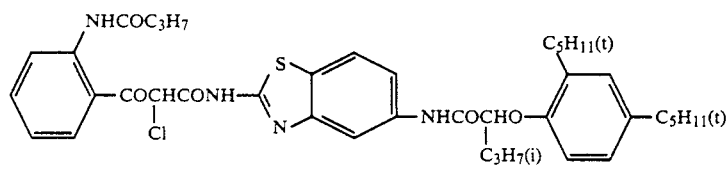 41.

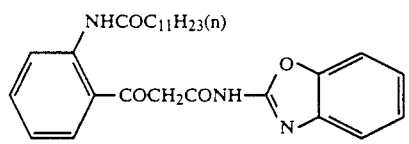 42.

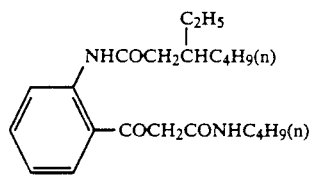 43.

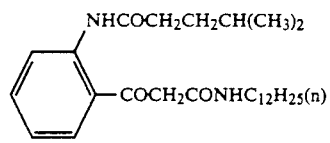 44.

SYNTHESIS EXAMPLES

Synthesis of ethyl o-butanamidobenzoylacetate

In 30 ml of toluene, 9.40 g of diethyl carbonate was dissolved. To this solution, 2.08 g of sodium hydride (60% content) was added, followed by heating at 70° C. While stirring the solution, 4.10 g of 2-butaneamidoacetophenone was added little by little over a period of 20 minutes.

Then, reaction was carried out at 80° C. for 2 hours. After cooling at room temperature, 3.2 g of glacial acetic acid was added, followed by the addition of 250ml of ice water and extraction with ethyl acetate.

After being thoroughly washed with water, the ethyl acetate layer was dehydrated with anhydrous magnesium sulfate and concentrated to yield 5.54 g of a light brown oily substance. This residue was used for the next reaction without any purification.

SYNTHESIS OF EXAMPLE COMPOUND 1

Synthesis of α-(o-butanamidobenzoyl)-2-chloro-5-dodecyloxycarbonylacetoanilide

In 100 ml of xylene, 5.45 g of crude ethyl o-butanamidobenzoylacetate and 8.04 g of 2-chloro-5-dodecyloxycarbonylaniline were mixed, followed by boiling at 3 hours. After the xylene was distilled off under reduced pressure, acetonitrile was added to cause crystallization. The resulting crystal was once collected by filtration and then recrystallized from acetonitrile. Yield=4.35 g. Melting point=99 to 100° C. The obtained substance was identified by NMR and mass spectrometry.

SYNTHESIS OF EXAMPLE COMPOUND 2

Synthesis of α-(o-butanamidobenzoyl)-α-chloro-2-chloro-5-dodecyloxycarbonylacetoanilide In 100 ml of ethyl acetate, 2.86 g of Example Compound 1 was dissolved. To this solution, 0.66 g of N-chlorosuccinic imide was added, followed by stirring at room temperature for 24 hours.

Then, water was added, and the ethyl acetate layer was thoroughly washed with water. After 3 times of water washing, the ethyl acetate layer was dehydrated with anhydrous sodium sulfate and concentrated under reduced pressure. The resulting oily residue was recrystallized with n-hexane to yield a white crystal. Yield=2.38 g. The obtained substance was identified by NMR and mass spectrometry.

SYNTHESIS OF EXAMPLE COMPOUND 3

Synthesis of α-(o-butanamidobenzoyl)-α-(N-benzylhydantoinyl)-2-chloro-5-dodecyloxycarbonylacetoanilide Two grams of Example Compound 2, 0.87 g of N-benzylhydantoin potassium salt and 100 ml of acetonitrile were mixed together, followed by boiling reflux for 5 hours. After cooling, the insoluble substance was filtered, and the acetonitrile was distilled off under reduced pressure.

Then, the residue was dissolved in ethyl acetate, and the ethyl acetate layer was thoroughly washed with water. After being thoroughly dehydrated with anhydrous magnesium sulfate, the ethyl acetate layer was concentrated under reduced pressure to yield a brown oily substance. This substance was purified via column chromatography and aspirated using a vacuum pump to yield an almost colorless caramel-like or amorphous solid substance.

This substance was identified by NMR and mass spectrometry.

Synthesis of ethyl o-benzenesulfonamidobenzoylacetate

In dehydrated toluene, 5.48 g of acetoacetate was dissolved. To this solution, 0.98 g of metallic sodium was added, followed by stirring at 80° C. for 5 hours.

Then, 15.4 g of o-benzenesulfonamidobenzoyl chloride was added little by little over a period of 30 minutes, followed by stirring with heating at 100° C. for 20 hours. After cooling, the reaction mixture was poured over ice water. After being washed with 200 ml of a 2.5% aqueous solution of sodium bicarbonate, the toluene layer was thoroughly washed with a sodium chloride solution.

Then, after the toluene layer was dehydrated with anhydrous magnesium sulfate, the toluene was distilled off under reduced pressure. An oily substance was obtained.

Then, this oily residue was mixed with 1.2 g of ammonium chloride, 1.0 ml of aqueous ammonia and 4 ml of water, followed by stirring for 2 hours while keeping the temperature not exceeding 45° C. After reaction, the reaction product was extracted with 300 ml of ethyl acetate. After being dehydrated with anhydrous magnesium sulfate, the ethyl acetate layer was concentrated. The resulting concentrate residue was recrystallized with n-hexane to yield 2.6 g of the desired product in the form of a white crystal. (Identified by NMR and spectrometry.)

SYNTHESIS OF EXAMPLE COMPOUND 17

A mixture of 1.74 g of the ethyl o-benzenesulfonamidobenzoylacetate described above, 3.50 g of 2-chloro-5-(dodecyloxycarbonyl)aniline and 50 ml of xylene was prepared and boiled for 3 hours. After concentration under reduced pressure, purification was carried out via column chromatography. A white amorphous solid of 2.03 g of was obtained, and it was identified by NMR and mass spectrometry.

SYNTHESIS OF EXAMPLE COMPOUND 34

Synthesis of 2-anilino-5-nitroacetophenone

Ten grams of 2-chloro-5-nitroacetophenone, 10 g of aniline and 10 g of anhydrous potassium carbonate were stirred with heating at 125° to 135° C. for 6 hours. The mixture was allowed to cool slightly and while it was still hot, 30 ml of alcohol was added with stirring. The mixture was allowed to stand for one night, and the precipitated yellow-brown crystal was filtered off, and 14.8 g of crude substance was obtained. The substance was recrystallized using 500 ml of alcohol, thus 10.1 g of the example compound was obtained, and whose melting point was 130° to 132° C.

SYNTHESIS OF 2-ANILINO-5-AMINOACETOPHENONE 5.12 grams of the so-obtained 2-anilino-5-nitroacetophenone was mixed with 200 ml of alcohol and 0.5 g of palladium/carbon catalyst, thereby the mixture was subjected to catalytic reduction at normal pressure. The reaction ceased when the material had absorbed approx. 1.39 l of hydrogen, and uniformly yellow solution was obtained. The catalyst was filtered out, and then the solution was condensed, leaving oil which was used in the following synthesis step.

SYNTHESIS OF 2-ANILINO-5-{2-(2,4-DI-T-AMYLPHENOXY)-3-METHYLBUTANEAMIDO}ACETOPHENONE)

The so-obtained crude amine was mixed with 150 ml of acetonitrile and 2.0 g of pyridine, and 7.04 g of 2-(2,4-di-t-amylphenoxy)-3-methyl-butylic acid chloride was added dropwise with stirring. As a result, the mixture gradually generated heat. After completion of addition dropwise, the solution was boiled and refluxed for approx. 1 hour, and then concentrated under reduced pressure. The concentrate was extracted using ethyl acetate, and was rinsed with diluted chloric acid, and then further rinsed twice with saturated salt water. The ethyl acetate layer was dried with magnesium sulfate, and then the residue was concentrated. The remaining oil was purified by column chromatography, thus 11.0 g of target material, in the form of pale brown caramel, was obtained, and was identified by mass spectrometry.

SYNTHESIS OF 2-ANILINO-5-{2-(2,4-DI-T-AMYLPHENOXY)-3-METHYLBUTANEAMIDO}BENZOYL ACETATE ETHYL ESTER

In 60 ml of toluene were dissolved 10.8 grams of 2-anilino-5-{2-(2,4-di-t-amylphenoxy)-3-methyl-butaneamido}-acetophenone and 9.40 g of diethyl carbonate, and 2.08 g of sodium hydride (60% content) was added, thereby the mixture was subjected to reaction with stirring at 80° C. for 3 hours. After cooling, a small amount of glacial acetic acid was added, and then, the mixture was poured in 300 ml of ice-cold water. Then, the reaction product was extracted with ethyl acetate. The ethyl acetate layer was thoroughly rinsed with water, and the product was dehydrated with anhydrous magnesium sulfate to concentrate the ethyl acetate layer. The residual caramel-like product was not purified, but identified by mass spectrometry and was used for the reaction below. The amount of product was 11.5 g.

SYNTHESIS OF EXAMPLE COMPOUND 34

To 50 ml of xylene were added 6.14 grams of the so-obtained benzoyl acetate ethyl ester and 2.43 g of 2,4-dichloroaniline, and the mixture was boiled for 4 hours. After xylene was removed vacuum-distillation, the residual caramel-like product was dissolved in ethyl acetate, and rinsed with diluted chloric acid, and then, thoroughly rinsed with saturated salt water. The resultant product was dehydrated with anhydrous magnesium sulfate to concentrate the ethyl acetate layer. The residual caramel-like product was purified by column chromatography to obtain 3.2 g of caramel-like product. This product was identified as the intended Example Compound 34 by mass spectrometry and NMR.

The yellow coupler of the present invention is used in a silver halide emulsion layer, mainly in a blue-sensitive silver halide emulsion layer. The amount of its addition is $2 \times 10^{-3}$ to $8 \times 10^{-1}$ mol, preferably $1 \times 10^{-2}$ to $5 \times 10^{-1}$ mol, per mol silver halide.

Various methods are available for adding the yellow coupler of the present invention to a silver halide emulsion layer. For example, the yellow coupler is dissolved in a high boiling organic solvent having a boiling point of not less than 150° C. such as an alkyl phthalate (e.g., dibutyl phthalate, dioctyl phthalate) or a phosphate (e.g., diphenyl phosphate, triphenyl phosphate, tricresyl phosphate, dioctylbutyl phosphate) and/or a low boiling organic solvent having a boiling point of 30° to 150° C. (e.g., ethyl acetate, butyl acetate, ethyl propionate, sec-butylalcohol, methyl isobutyl ketone, methyl cellosolve acetate), and then dispersed in hydrophilic colloid. Usually, it is preferable to use these high boiling and low boiling organic solvents in mixture.

Although no limitation is posed on the choice of a type of silver halide grains used in a silver halide emulsion layer of the silver halide photographic light-sensitive material of the present invention, it is preferable to use silver chloride, silver chlorobromide or silver chloroiodide for a light-sensitive material requiring particularly quick developability, such as color photographic paper.

The particularly preferred silver halide grains as described above are silver halide grains for quick processing having a silver chloride content of not less than 90 mol%.

These silver halide grains for quick processing have a silver chloride content of not less than 90 mol%, and preferably have a silver bromide content of not more than 5 mol% and a silver iodide content of not more than 0.5 mol%. More preferred are silver chlorobromide grains having a silver bromide content of 0.1 to 1.0 mol%.

This type of silver halide grains for quick processing may be used singly or in mixture with another type of silver halide grains with a different silver halide composition. It may also be used in mixture with a type of silver halide grains having a silver chloride content of less than 10 mol%.

In the silver halide emulsion layers containing silver halide grains for quick processing, the ratio of this type of silver halide grains for quick processing to the total amount of silver halide grains contained in these emulsion layers is preferably not less than 60% by weight, more preferably not less than 80% by weight.

The silver halide emulsion used for the present invention may be a polydisperse type with a broad range of average grain size distribution, but preference is given to a monodisperse emulsion.

The emulsion containing these silver halide grains may be chemically sensitized with active gelatin, a sulfur sensitizer, a selenium sensitizer, a reduction sensitizer, a precious metal sensitizer or another sensitizer.

The silver halide used for the present invention may be optically sensitized by the addition of an appropriate sensitizing dye for the purpose of providing sensitivity in a desired wavelength region.

The silver halide photographic light-sensitive material of the present invention, comprising as above, may be a color negative film or positive film, color photographic paper, or the like, but the effect of the present invention is enhanced when it is applied to a color photographic paper used to be directly viewed.

The silver halide photographic light-sensitive material of the present invention, including such a color photographic paper, is a multicolor silver halide photographic light-sensitive material, and has a structure in which silver halide emulsion layers respectively containing a magenta coupler, a yellow coupler and a cyan coupler, and a non-light-sensitive layer, laminated in an appropriate number and order, for the purpose of subtractive color reproduction. This number and order of layers may be altered as desired according to the key performance and purpose of use.

It is preferable that the layer structure of the silver halide photographic light-sensitive material of the present invention is such that a yellow dye forming layer, an interlayer, a magenta dye forming layer, an interlayer, a cyan dye forming layer, an interlayer and a protective layer are arranged on the support in this order from the support.

The silver halide photographic light-sensitive material of the present invention can be contained as desired with an anti-color fogging agent, an image stabilizer, a hardener, a plasticizer, a polymer latex, an ultraviolet absorbent, a formalin scavenger, a mordant, a development accelerator, a development retarder, a fluorescent brightening agent, a matting agent, an antistatic agent, a surfactant, and other additives.

Various color developing processes are applicable to the development of the silver halide photographic light-sensitive material of the present invention.

EXAMPLES

Example 1

Ten grams of the coupler Y-1 described below, 10 g of dioctyl phthalate and 20 ml of ethyl acetate were completely dissolved by heating at 50° C. This solution was mixed with 100 ml of an aqueous solution containing 10 g of gelatin and 0.4 g of Alkanol XC, sodium diisopropylnaphthalenesulfonate, produced by Dupont. After stirring, the mixture was finely emulsified and dispersed by ultrasonication. The resulting coupler dispersion was added to 400 g of a photographic emulsion containing 35 g of silver chlorobromide having the silver chloride content of 99% and 40 g of gelatin. After adding 40 ml of an aqueous solution of 2,4-dichloro-6-hydroxy-s-triazine sodium as a hardener and adjusting the pH to 6.0, the mixture was uniformly coated on a subbed triacetyl cellulose film base to prepare sample 1.

Other samples were prepared in the same manner as with sample 1 except for the coupler Y-1 was replaced with an equimolar of a yellow coupler listed in Table 1.

These samples were exposed to light through a sensitometric optical wedge, and then subjected to the following color development, bleach-fixation and stabilization processes, and the sensitivity and maximum density were determined.

Also, each processed sample was subjected to light irradiation using a xenon fademeter for 9 days, and the light-fastness of yellow images was assessed. The results are shown in Table 2.

| Process | Temperature | Duration |
|---|---|---|
| Color development | 35° C. | 45 seconds |
| Bleach-fixation | 35° C. | 45 seconds |
| Stabilization | 35° C. | 1 minute 30 seconds |
| Drying | 60 to 80° C. | 2 minutes |

The compositions of respective processing solutions are as follows:

| Color developer | |
|---|---|
| Pure water | 800 ml |
| Triethanolamine | 11 ml |
| N,N-diethylhydroxylamine (85% aqueous solution) | 6 ml |
| Potassium chloride | 2.3 g |
| Potassium sulfite | 0.3 g |
| Potassium carbonate | 30 g |
| Sodium tetrapolyphosphate | 2.0 g |
| N-ethyl-N-$\beta$-methanesulfonamidoethyl-3-ethyl-4-aminoaniline sulfate | 5.2 g |

Pure water was added to reach a total volume of 1 l, and pH was adjusted to 10.1 with 20% potassium hydroxide or 10% dilute sulfuric acid.

| Bleach-fixer | |
|---|---|
| Pure water | 800 ml |
| Iron (III) ammonium ethylenediaminetetraacetate | 65 g |
| Disodium ethylenediaminetetraacetate | 5 g |
| Ammonium thiosulfate | 60 g |
| Sodium hydrogen sulfite | 10 g |
| Sodium metabisulfite | 2 g |
| Sodium chloride | 10 g |

Pure water was added to reach a total volume of 1 l, and pH was adjusted to 5.6 with dilute sulfuric acid.

| Stabilizer | |
|---|---|
| 5-chloro-2-methyl-4-isothiazolin-3-one | 1.0 g |
| 1-hydroxyethylidene-1,1-diphosphonic acid | 2.0 g |

Pure water was added to reach a total volume of 1 l, and pH was adjusted to 7.0 with sulfuric acid or potassium hydroxide.

TABLE 1

| Sample No. | Yellow coupler | Sensitivity[1] | Maximum density | Light fastness[2] |
|---|---|---|---|---|
| 1(Comparative) | Y-1 | 100 | 1.25 | 0.48 |
| 2(Inventive) | Example Compound 3 | 104 | 1.30 | 0.50 |
| 3(Inventive) | Example Compound 4 | 105 | 1.30 | 0.52 |
| 4(Inventive) | Example Compound 20 | 103 | 1.32 | 0.53 |
| 5(Inventive) | Example Compound 6 | 102 | 1.30 | 0.50 |
| 6(Inventive) | Example Compound 12 | 102 | 1.28 | 0.50 |
| 7(Inventive) | Example Compound 16 | 101 | 1.30 | 0.52 |

[1]Percent ratio relative to the sensitivity of Sample 1
[2]Density after deterioration at a portion with an initial density of 1.0

Y-1

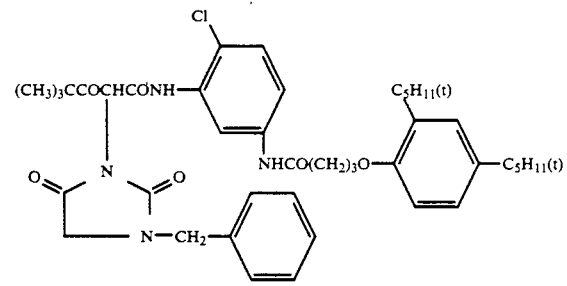

As is evident from the results shown in Table 1, the silver halide photographic light-sensitive material incorporating the compound of the present invention as a yellow coupler offers excellent color forming ability and light-fastness.

EXAMPLE 2 (preparation of silver halide emulsions)

The three kinds of silver halide emulsions shown in Table 2 were prepared by the neutral double jet precipitation method.

TABLE 2

| Emulsion number | AgCl % | AgBr % | Average grain size ($\mu$m) | Chemical sensitizer | Spectral sensitizing dye |
|---|---|---|---|---|---|
| Em - 1 | 99.5 | 0.5 | 0.67 | Sodium thiosulfate *1 | SD - 1 *3 |
| Em - 2 | 99.5 | 0.5 | 0.46 | | SD - 2 *4 |
| Em - 3 | 99.5 | 0.5 | 0.43 | Chloroauric acid *2 | SD - 3 *5 |

*1 Added at 2 mg per mol silver halide.
*2 Added at $5 \times 10^{-5}$ mol per mol silver halide.
*3 Added at 0.9 mmol per mol silver halide.
*4 Added at 0.7 mmol per mol silver halide.
*5 Added at 0.2 mmol per mol silver halide.

After completion of chemical sensitization, the following STB-1 was added to each emulsion as an emulsion stabilizer at $5 \times 10^{-3}$ mol per mol silver halide.

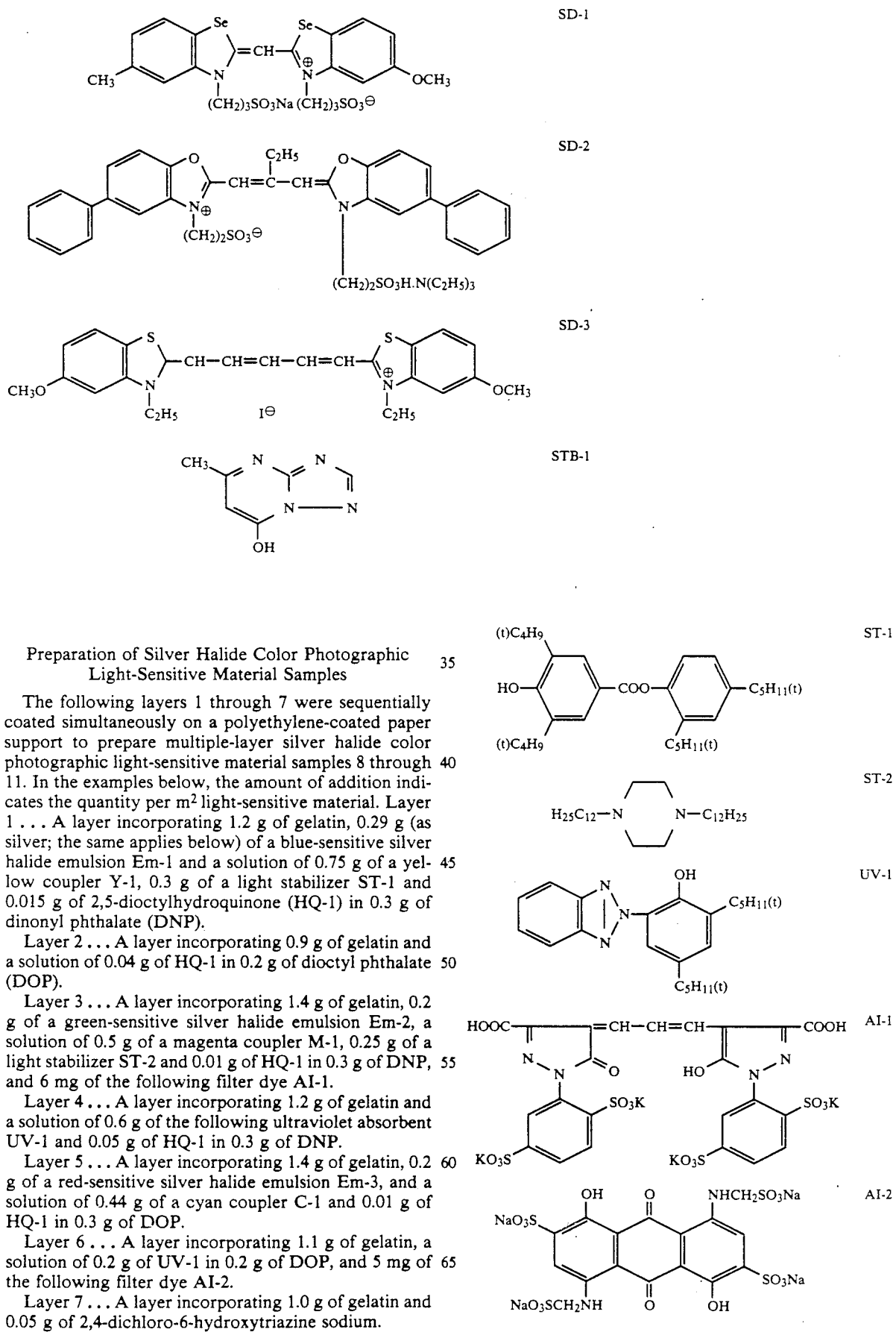

Preparation of Silver Halide Color Photographic Light-Sensitive Material Samples The following layers 1 through 7 were sequentially coated simultaneously on a polyethylene-coated paper support to prepare multiple-layer silver halide color photographic light-sensitive material samples 8 through 11. In the examples below, the amount of addition indicates the quantity per m² light-sensitive material. Layer 1 ... A layer incorporating 1.2 g of gelatin, 0.29 g (as silver; the same applies below) of a blue-sensitive silver halide emulsion Em-1 and a solution of 0.75 g of a yellow coupler Y-1, 0.3 g of a light stabilizer ST-1 and 0.015 g of 2,5-dioctylhydroquinone (HQ-1) in 0.3 g of dinonyl phthalate (DNP).

Layer 2 ... A layer incorporating 0.9 g of gelatin and a solution of 0.04 g of HQ-1 in 0.2 g of dioctyl phthalate (DOP).

Layer 3 ... A layer incorporating 1.4 g of gelatin, 0.2 g of a green-sensitive silver halide emulsion Em-2, a solution of 0.5 g of a magenta coupler M-1, 0.25 g of a light stabilizer ST-2 and 0.01 g of HQ-1 in 0.3 g of DNP, and 6 mg of the following filter dye AI-1.

Layer 4 ... A layer incorporating 1.2 g of gelatin and a solution of 0.6 g of the following ultraviolet absorbent UV-1 and 0.05 g of HQ-1 in 0.3 g of DNP.

Layer 5 ... A layer incorporating 1.4 g of gelatin, 0.2 g of a red-sensitive silver halide emulsion Em-3, and a solution of 0.44 g of a cyan coupler C-1 and 0.01 g of HQ-1 in 0.3 g of DOP.

Layer 6 ... A layer incorporating 1.1 g of gelatin, a solution of 0.2 g of UV-1 in 0.2 g of DOP, and 5 mg of the following filter dye AI-2.

Layer 7 ... A layer incorporating 1.0 g of gelatin and 0.05 g of 2,4-dichloro-6-hydroxytriazine sodium.

-continued

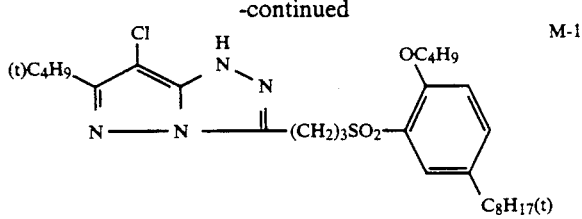
M-1

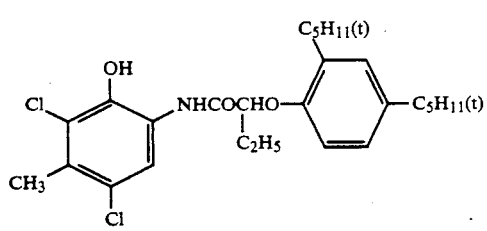
C-1

Also, samples 9, 10 and 11 were prepared in the same manner as with sample 8 except that the yellow coupler Y-1 for layer 1 of sample 8 was replaced with an equimolar of a coupler of the present invention shown in Table 3.

The samples obtained were each subjected to exposure with an optical wedge using a sensitometer KS-7 model (produced by Konishiroku Photo Industry Co., Ltd.) and processed in accordance with the following color photographic processes. Then, the maximum density $D_{max}$ of the blue-sensitive emulsion layer was determined using an optical densitometer (produced by Konica Corporation, PDA-65 model).

The samples were each stored at 85° C. and a relative humidity of 60% for 20 days, and then the dye image residual ratio (%) at the portion with an initial density of 1.0 was determined to assess the dark discoloration.

The results are shown in table 3.

The processing solutions used were the same as those in Example 1

TABLE 3

| Process | Temperature | Duration |
| --- | --- | --- |
| Color development | 34.7 ± 0.3° C. | 45 seconds |
| Bleach-fixation | 34.7 ± 0.5° C. | 45 seconds |
| Stabilization | 30 to 34° C. | 90 seconds |
| Drying | 60 to 80° C. | 60 seconds |

| Sample No. | Yellow coupler | Maximum density | Dark discoloration |
| --- | --- | --- | --- |
| 1 (Comparative) | Y - 1 | 2.30 | 98 |
| 9 (Inventive) | Example Compound 3 | 2.32 | 99 |
| 10 (Comparative) | Example Compound 4 | 2.33 | 98 |
| 11 (Comparative) | Example Compound 16 | 2.32 | 98 |

As seen from the results shown in Table 3, samples 9, 10 and 11 are comparable or superior to sample 1, incorporating a conventional yellow coupler, in $D_{max}$ and dark discoloration.

EXAMPLE 3

Photographs of the color checker produced by Macbeth Co. were taken using Konica GX-100 and subjected to ordinary developing processes to yield a color negative film. Using this film, images were printed on samples 8 through 11 obtained in Example 2 with neutral gray adjustment.

In comparison with comparative sample 8, samples 9, 10 and 11, prepared in accordance with the present invention, reproduced visually very clear yellow, yellowish-green and other colors.

EXAMPLE 4

Samples 12 through 19 were prepared in a manner identical to that in Example 1 except in that the support, i.e. a triacetyl cellulose film base, was replaced with polyethylene-laminated paper.

These samples were subjected to exposure with a sensitometric optical wedge, and then subjected to color developing, bleach-fixing and stabilizing as in Example 1 to evaluate their sensitivity and maximum density. Additionally, each treated sample was irradiated with xenon fademeter for 4 days to evaluate light fastness of yellow image. The results are summarized in Table 4.

TABLE 4

| Sample No. | Yellow coupler | Sensitivity | Maximum density | Light fastness |
| --- | --- | --- | --- | --- |
| 12 (Comparative) | Y - 1 | 100 | 2.73 | 0.42 |
| 13 (Inventive) | Example Compound 3 | 104 | 2.85 | 0.46 |
| 14 (Inventive) | Example Compound 6 | 105 | 2.88 | 0.45 |
| 15 (Inventive) | Example Compound 12 | 103 | 2.78 | 0.45 |
| 16 (Inventive) | Example Compound 16 | 105 | 2.84 | 0.47 |
| 17 (Inventive) | Example Compound 31 | 106 | 2.86 | 0.53 |
| 18 (Inventive) | Example Compound 35 | 106 | 2.85 | 0.54 |
| 19 (Inventive) | Example Compound 38 | 102 | 2.78 | 0.45 |

As can be understood from the results in Table 4, the samples that are photographic materials having reflective support are excellent in sensitivity, maximum density, and light fastness since they incorporate yellow coupler of the invention.

What is claimed is:

1. A silver halide color photographic light-sensitive material comprising a support and a silver halide emulsion layer containing a yellow coupler represented by the following Formula I:

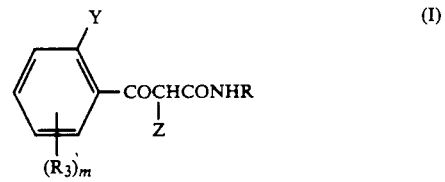

wherein Y is a hydrogen bond donating group; R is an alkyl group, an aryl group or a heterocyclic group; $R_3$ is a halogen atom, hydroxyl group, nitro group or a monovalent organic group; m is an integer of 0 to 4, provided that the groups represented by $R_3$ may be the same or different when m is 2 or more; and Z is a hydrogen atom or a substituent capable of splitting off upon rection with the oxidation product of an aromatic primary amine color developing agent.

2. A material of claim 1, wherein said monovalent organic group represented by $R_3$ is an alkyl group, an aryl group, an alkoxy group, an aryloxy group, an alkylamido group, an arylamido group, an alkylsulfonamido group, an arylsulfonamido group, alkylcarbamoyl group, an arylcarbamoyl group, an alkoxycarbonyl group, an aryloxycarbonyl group, an alkanoyloxy group, an arylcarbonyloxy group or a dialkylamino group.

3. A material of claim 1, wherein said yellow coupler is represented by the following Formula II:

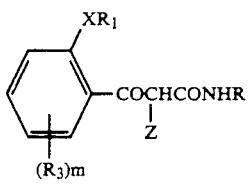

wherein R, $R_3$, Z, and m are the same as defined in Formula I; X is —NH— or —O—; and $R_1$ is an aryl group, a —$COR_4$ group or a —$SO_2R_4$ group when X is —NH—, where $R_4$ is an alkyl group, an aryl group, an alky amino group, a dialkylamino group, an arylamino group, an alkoxy group or an aryloxy group; and $R_1$ is a hydrogen atom when X is —O—.

4. A material of claim 3, wherein said yellow coupler is represented by the following Formula III:

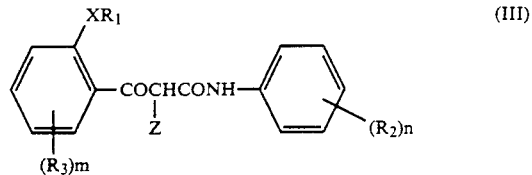

wherein X, $R_1$, $R_3$, Z and m are the same as defined in Formula 11; $R_2$ is a halogen atom or a monovalent organic group; and n is an integer of 0 to 5 provided that the groups represented by $R_2$ may be different from each other when n is 2 or more.

5. A material of claim 4, wherein said monovalent organic group represented by $R_2$ is an alkyl group, an aryl group, an alkoxy group, an aryloxy group, an alkylamido group, an arylamido group, an alkylsulfonamido group, an arylsulfonamido group, alkylcarbamoyl group, an arylcarbamoyl group, an alkoxycarbonyl group, an aryloxycarbonyl group, an alkanoyloxy group, an arylcarbonyloxy group or a dialkylamino group.

6. A material of claim 1, wherein said yellow coupler is contained in a blue-sensitive silver halide emulsion layer.

7. A material of claim 1, wherein said yellow coupler is contained said silver halide emulsion layer in an amount of from $2 \times 10^{-3}$ moles to $8 \times 10^{-1}$ moles per mole of silver halide contained in said silver halide emulsion layer.

8. A material of claim 1, wherein said silver halide emulsion layer comprises silver halide grains having a silver chloride content of not less than 90 mole%.

9. A material of claim 8, wherein said silver halide grains are silver chlorobromide grains having a silver bromide content of from 0.1 to 1.0 mole%.

* * * * *